(12) United States Patent
Rhea (10) Patent No.: US 10,152,898 B2
(45) Date of Patent: Dec. 11, 2018

(54) VIRTUAL REALITY TRAINING TO ENHANCE PHYSICAL REHABILITATION

(71) Applicant: THE UNIVERSITY OF NORTH CAROLINA AT GREENSBORO, Greensboro, NC (US)

(72) Inventor: Christopher K. Rhea, Greensboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 75 days.

(21) Appl. No.: 14/427,434

(22) PCT Filed: Sep. 13, 2013

(86) PCT No.: PCT/US2013/059805
§ 371 (c)(1),
(2) Date: Mar. 11, 2015

(87) PCT Pub. No.: WO2014/043572
PCT Pub. Date: Mar. 20, 2014

(65) Prior Publication Data
US 2015/0213729 A1    Jul. 30, 2015

Related U.S. Application Data

(60) Provisional application No. 61/700,906, filed on Sep. 14, 2012.

(51) Int. Cl.
*G09B 9/00*    (2006.01)
*G06F 19/00*    (2018.01)
*G09B 5/02*    (2006.01)

(52) U.S. Cl.
CPC ............ *G09B 9/00* (2013.01); *G06F 19/3481* (2013.01); *G09B 5/02* (2013.01)

(58) Field of Classification Search
CPC ........................................................ G09B 9/00
USPC ........................................................ 434/247
See application file for complete search history.

(56) References Cited

U.S. PATENT DOCUMENTS

| | | | | |
|---|---|---|---|---|
| 6,774,885 B1* | 8/2004 | Even-Zohar | ......... | A61B 5/1036 345/156 |
| 2009/0148000 A1* | 6/2009 | Madsen | ................ | G06T 7/2033 382/107 |
| 2009/0220124 A1* | 9/2009 | Siegel | ................ | G06K 9/00342 382/103 |

(Continued)

OTHER PUBLICATIONS

Koritnik et al, Virtual environment for lower-extremities training, 2008, Gait & Posture, 27, p. 323-330.*

(Continued)

*Primary Examiner* — Thomas Hong
(74) *Attorney, Agent, or Firm* — Kilpatrick Townsend & Stockton LLP (57) ABSTRACT

Embodiments of the disclosed invention encompass physiological and behavioral measurement techniques that can index dynamical diseases. Embodiments include a system and method for continuously measuring locomotor patterns which may be in combination with classic summary measures of performance, compared to summary measures alone. A unique classification of mathematics may be employed to prescribe certain patterns which correspond to locomotor patterns of a test subject.

19 Claims, 7 Drawing Sheets

(56) References Cited

U.S. PATENT DOCUMENTS

| | | | |
|---|---|---|---|
| 2009/0298650 A1* | 12/2009 | Kutliroff | A63B 71/0622 |
| | | | 482/8 |
| 2011/0184225 A1* | 7/2011 | Whitall | A63B 69/0028 |
| | | | 600/28 |
| 2012/0119904 A1* | 5/2012 | Coleman Boone | A61B 5/112 |
| | | | 340/539.12 |
| 2012/0183940 A1* | 7/2012 | Aragones | G06F 19/3437 |
| | | | 434/247 |
| 2012/0212505 A1* | 8/2012 | Burroughs | G06F 19/3481 |
| | | | 345/629 |
| 2012/0253201 A1* | 10/2012 | Reinhold | A61B 5/1113 |
| | | | 600/473 |
| 2013/0123667 A1* | 5/2013 | Komatireddy | A61B 5/0002 |
| | | | 600/595 |
| 2014/0276130 A1* | 9/2014 | Mirelman | A61B 5/744 |
| | | | 600/483 |

OTHER PUBLICATIONS

Katsavelis et al, The Effect of Virtual Reality on Gait Variability, 2010, Nonlinear Dynamics, Psychology, and Life Sciences, vol. 14, No. 3, p. 239-256.*

The effect of real and virtual visual cues on walking in Parkinson's disease, 2011, Journal of Neurology, 258, p. 991-1000.*

Arias P, Robles-Garcí a V, Sanmartí n G, Flores J, Cudeiro J (2012) Virtual Reality as a Tool for Evaluation of Repetitive Rhythmic Movements in the Elderly and Parkinson's Disease Patients.*

The Effect of Virtual Reality on Gait Variability, 2010, Nonlinear Dynamics, Psychology, and Life Sciences, 14(3): 239-256.*

Blin et al., 1990, Quantitative analysis of gait in Parkinson patients: increased variability of stride length, J. Neurol. Sci., 98(1):91-7.

Geruschat et al., 1998, Traditional Measures of Mobility Performance and Retinitis Pigmentosa, Optometry and Vision Science, 75(7):525-537.

Glass & Mackey, 1979, Pathological conditions resulting from instabilities in physiological control systems, Ann N Y Acad Sci., 316:214-35.

Grabiner et al., 2001, Age-related changes in spatial and temporal gait variables, Arch Phys Med Rehabil., 2001, 82(1):31-5.

Haymes et al., 1996, Mobility of People with Retinitis Pigmentosa as a Function of Vision and Psychological Variables, Optometry and Vision Science, (73)10:621-637.

Kuyk et al., 1996, Environmental variables and mobility performance in adults with low vision. Journal of the American Optometric Association, 67(7):403-409.

Lovie-Kitchin et al., 1990, What Areas of the Visual Field are Important for Mobility in Low Vision Patients? Clin. Vision Sci., 5(3):349-263.

Mackey & Glass, 1977, Oscillation and chaos in physiological control systems, Science, 197(4300):287-9.

Owings & Grabiner, 2004, Variability of step kinematics in young and older adults, Gait Posture, 20(1):26-9.

Peng et al., 1995, Quantification of scaling exponents and crossover phenomena in nonstationary heartbeat time series, Chaos. 1995;5(1):82-7.

Spaulding et al., 2003, The influence of external orthotic support on the adaptive gait characteristics of individuals with chronically unstable ankles, Gait Posture. Apr. 2003; 17(2):152-8.

Turano et al., 2001, Direction of gaze while walking a simple route: persons with normal vision and persons with retinitis pigmentosa, Optom Vis Sci., 78(9):667-75.

von Porat et al., 2006, Knee kinematics and kinetics during gait, step and hop in males with a 16 years old ACL injury compared with matched controls, *Knee Surg Sports Traumatol Arthrosc.*, Jun; 14(6):546-54.

Webster et al., 2006, Gait variability in community dwelling adults with Alzheimer disease, Alzheimer Dis Assoc Disord., 20(1):37-40.

* cited by examiner

VIRTUAL REALITY TRAINING TO ENHANCE PHYSICAL REHABILITATION

CROSS-REFERENCE TO RELATED APPLICATIONS

The present application claims the benefit of priority to U.S. Provisional Patent Application No. 61/700,906, filed Sep. 14, 2012, which is incorporated by reference in its entirety as though fully set forth herein.

FIELD OF THE INVENTION

The present invention relates to employing virtual reality platforms to enhance movement, and in particular rehabilitation, and in particular, extending this methodology to patients with a variety of locomotor disorders due to structural or neurological insults.

BACKGROUND OF THE INVENTION

A person's mobility depends on an adaptively functioning perception-action system. Consequently, mobility limitations can arise from a host of pathologies and injuries that affect various loci in this system, from sensory receptors to cortical areas to musculo-skeletal components. However, such deficits typically impact the function of the system as a whole, and require adaption of perceptual-motor control strategies. For example, a chronic knee injury may alter the actions afforded by the environment and require the remapping of visual information to gait control variables in order to generate adaptive locomotion. Rehabilitation may thus not only involve strengthening muscles and retraining motor patterns, but relearning whole perceptual-motor control relations.

Mobility deficits may persist indefinitely and often deteriorate over time. For instance, at 12 months post-stroke, patients suffering from hemiplegia may exhibit motor deficits in the form of longer gait cycles with decreased cadences, and may result in a 50% reduction in walking speed compared to the gait patterns of unaffected control participants (Olney & Richards, *Gait Posture* 4: 136-138, 1996; von Schroeder, Coutts, Lyden, Billings, & Nickel, *J Rehabil Res Dev*. 32: 25-31, 1995). In another example, patients suffering from Parkinson's disease frequently exhibit freezing gait—a term that encompasses both the inability of the patient to initiate or sustain a walking gait, and shuffling forward with small steps as their legs exhibit muscle trembling—and these symptoms worsen as the disease progresses (Bloem, Hausdorff, Visser & Giladi, *Move Disord*. 19: 871-84, 2004; Riess, *Ios Press*, 200-208, 1998). Mobility issues are also the typical sequelae of sensory deficits such as "tunnel vision" due to conditions like retinitis pigmentosa (RP)—a group of hereditary disorders characterized by retinal pigmentary degeneration that often leads to progressive visual field loss (Geruschat, Turano & Stahl, *Optom Vis Sci*. 75:525-37, 1998; Haymes, Guest, Heyes & Johnston, *Optom Vis Sci*. 73:621-37, 1996; Kuyk, Elliott, Biehl & Fuhr, *J Am Optom Assoc*. 67: 403-9, 1996; Lovie-Kitchin, Mainstone, Robinson & Brown, *Clin Vis Sci* 5:249-263, 1990; Turano, Geruschat, Baker, Stahl, & Shapiro, *Optom Vis Sci*. 78:667-75, 2001).

This spectrum of deficits may detract from a patient's functional mobility by reducing their ability to adapt (prospectively and/or reactively) to normally varying environmental conditions during locomotion. Moreover, the basis of these deficits directly impacts the type and severity of such deficits, as well as the type of interventions that can be utilized to improve patient mobility. In direct response to these problems, researchers have started to employ virtual reality (VR) training interventions that may facilitate rehab of patients with mobility deficits.

The advent of VR as a tool for real-world training dates back to the mid-twentieth century and the early years of driving and flight simulators. These simulation environments, while far below the quality of today's visual displays, proved to be advantageous to the learner due to the safe training environments the simulations provided. More recently, these training environments have proven beneficial in the transferability of user-learned skills from the simulated environment to the real world. The development of VR technology of today has included, for example, contemporary displays boasting higher quality resolutions, wide-angle field of views and increased portability. This has led to the evolution of new VR research and training applications in many different arenas. This is true of clinical assessment and rehabilitation, as the field has recognized some potential advantages of incorporating VR technologies into patient training Unfortunately, many of the early desktop VR clinical interventions suffer from technological constraints in hardware and software that may limit their value as training tools for many clinical populations.

One of the major challenges facing VR-based assessment and rehabilitation is determining the type of VR installation to employ. This may require a greater understanding of the parameters needed to measure and/or access any locomotor deficiencies in patients in order to fully appreciate any defects and to treat the same. The hardware, such as visual displays and head tracking devices available, as well as systems for kinematic and kinetic measurement of movement, may strongly constrain the type of locomotor behavior permitted. For example, while over-ground walking may allow for the most natural interaction between the user and a virtual environment, space limitations may physically limit traditional systems.

Accordingly, a need exists for developing and refining new technological advancements to provide enhanced training tools that allow a user to navigate virtual environments. A need further exists to provided combined and improved visual displays, which serve to enhance the immersive nature of VR and efforts to introduce new behavioral measurement opportunities to facilitate the rehabilitation of patients.

SUMMARY OF THE INVENTION

In at least one aspect, the present invention provides a method of virtual reality training for a subject, comprising: (a) having a subject perform a motion; (b) measuring the subject's motion; (c) quantitatively characterizing the subject's measured motion to generate a movement signature; (d) comparing the subject's movement signature to a normative value for a movement signature derived from control subjects performing the same motion; and (e) having the subject observe a virtual environment while performing the motion to influence the subject's motion so as to align the subject's movement signature more closely to the normative movement signature.

In at least one aspect, the present invention provides a system for virtual reality training for a subject, comprising: (a) a station for having a subject perform a motion; (b) a station for measuring the subject's motion; (c) a station for quantitatively characterizing the subject's measured motion to generate a movement signature; (d) a station for comparing the subject's movement signature to a normative value for a movement signature derived from control subjects performing the same motion; and (e) a station for having the subject observe a virtual environment while performing the motion to influence the subject's motion so as to align the subject's movement signature more closely to the normative movement signature.

In at least one aspect, the present invention provides computer readable medium for performing the method comprising: (a) program code for measuring a subject's motion; (b) program code for quantitatively characterizing the subject's measured motion to generate a movement signature; (c) program code for comparing the subject's movement signature to a normative value for a movement signature derived from control subjects performing the same motion; (d) program code for manipulating a virtual environment while a subject performs the motion to influence the subject's motion so as to align the subject's movement signature more closely to the normative movement signature; and (e) program code for measuring change of the subject's movement signature.

In another aspect, the invention provides a method for virtual reality training, comprising: (a) having a subject perform a movement, wherein the subject's movement can be quantified as a movement signature; (b) comparing the subject's movement signature to a normative value movement signature derived from control subjects performing the same movement; (c) having a subject perform a movement while observing a virtual environment, wherein the virtual environment comprises a normative value movement signature derived from control subjects performing the same movement; and (d) having the subject attempt to synchronize the subject's movement to the virtual environment.

BRIEF DESCRIPTION OF THE DRAWINGS

The accompanying drawings, which are incorporated herein and constitute part of this specification, illustrate exemplary embodiments of the present invention and, together with the general description given above and the detailed description given below, serve to explain the features of the present invention.

DETAILED DESCRIPTION OF THE PREFERRED EMBODIMENTS

Definitions

Where the definition of terms departs from the commonly used meaning of the term, applicant intends to utilize the definitions provided below, unless specifically indicated. For purposes of the present invention, it should be noted that the singular forms, "a," "an" and "the," include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, the term "dynamical disease" refers to a physiological control system (e.g., the central nervous system) operating within some range of control parameters (e.g., frequency of stride-to-stride intervals) that, in turn, constrain the dynamics of the system and lead to abnormal (i.e., pathological) behavior (Mackey & Glass *Science* 197: 287-9, 1977; Glass & Mackey *Ann N Y Acad Sci.* 316: 214-35, 1979).

For purposes of the present invention, the term "detrended fluctuation analysis" (DFA) refers to an analytical tool for computing scaling exponents that relate a measure of variability, the detrended fluctuation function, to a time scale over which the function was computed (see Peng, Havlin, Stanley, and Goldberger *Chaos* 5: 82-87, 1995). In stochastic processes, chaos theory and time series analysis, DFA is a method for determining the statistical self-affinity of a signal. It is useful for analyzing time series that appear to be long-memory processes (diverging correlation time, e.g. power-law decaying autocorrelation function), also represented by fractal patterns. The obtained exponent is similar to the Hurst exponent, except that DFA may also be applied to signals whose underlying statistics (such as mean and variance) or dynamics are non-stationary (changing with time). It is related to measures based upon spectral techniques such as autocorrelation and Fourier transform. DFA may represent an extension of the (ordinary) fluctuation analysis (FA), which is affected by non-stationarities.

For purposes of the present invention, the term "avatar" refers to a personalized graphic file or rendering that represents a user.

For purposes of the present invention, the term "movement signature" refers to an electronically captured mathematical characterization or description of a subject's motion. Those skilled in the art will readily appreciate that any number of known mathematical concepts may be suitable for incorporation into the determination of a movement signature.

For purposes of the present invention, the term "classic summary measures" include metrics such as, for example, mean, standard deviation, and a coefficient of variation.

For purposes of the present invention, the term "F(n)" means the average fluctuation over a variety of time scales, where a time scale can be any increment of time.

For purposes of the present invention, the term "time scale" (or "box size") represents the number of data points being analyzed.

For purposes of the present invention, a "metronome" provides a stimulus at a set time interval over a defined duration of time. Typically the stimulus is an auditory stimulus, but a "visual metronome" is a visual stimulus which may be incorporated into a virtual environment (for example, a flashing square).

For purposes of the present invention, the term "noisy, visual metronome" represents an irregular visual metronome with variable intervals between beats.

For purposes of the present invention, the term "fractal pattern of dynamic variability" represents patterns within the beat variation.

For purposes of the present invention, the term "station" includes any suitable apparatus or collections of apparatuses suitable for carrying out the recited method. The stations need not be integrally connected or situated with respect to each other in any particular way.

For purposes of the present invention, the term "virtual reality" (VR) refers to a simulated environment, herein called the "virtual environment," that can simulate physical presence in places in the real world or imagined worlds. Typically VR environments are primarily visual experiences, displayed either on a screen, such as for example a projector screen, or through special displays such as, for example, head-mounted displays, but some simulations include additional sensory information, such as sound through speakers or headphones.

Description

In some embodiments, the present invention provides a method of virtual reality training for a subject, comprising: (a) having a subject perform a motion; (b) measuring the subject's motion; (c) quantitatively characterizing the subject's measured motion to generate a movement signature; (d) comparing the subject's movement signature to a normative value for a movement signature derived from control subjects performing the same motion; and (e) having the subject observe a virtual environment while performing the motion to influence the subject's motion so as to align the subject's movement signature more closely to the normative movement signature.

In some embodiments, the subject is instructed to synchronize a motion to a visual stimulus observed in the virtual environment. In some embodiments, the steps are repeated until the subject's movement signature reaches a predetermined value.

In some embodiments, the quantitative characterization to generate a movement signature comprises a measurement of variability of the motion over time. In some embodiments, the measurement of variability over time comprises an integrated time series. In some embodiments, the integrated time series is indexed by detrended fluctuation analysis.

In some embodiments, the subject performing a motion has a mobility deficit due to a neurological or structural insult. In some embodiments, the motion is a locomotor motion. In some embodiments, the motion is walking. In some embodiments, the motion is running. In some embodiments, the subject is in need of rehabilitation for functional mobility.

In some embodiments of the present invention, the virtual reality training facilitates recovery of the subject's functional mobility. In some embodiments, the virtual reality training comprises observation of a virtual environment by the subject. In some embodiments, the virtual environment comprises a visual stimulus. In some embodiments, the visual stimulus comprises discrete visual cues in the virtual environment. In some embodiments, the visual stimulus comprises continuous visual cues in the virtual environment.

In some embodiments of the present invention, the visual stimulus comprises an avatar. In some embodiments, the visual stimulus comprises a visual metronome. In some embodiments, the motion is a locomotor motion and the subject is instructed to synchronize heel strikes to the visual stimulus.

In some embodiments, the subject performs the locomotor motion on a treadmill. In some embodiments, the subject observes the virtual environment through a device worn by the subject.

In some embodiments, the subject performs the locomotor motion over ground. In some such embodiments, the subject performs the locomotor motion without causing the body to travel away from its starting point (i.e. stepping in place).

In some embodiments, the present invention comprises a system for virtual reality training for a subject, comprising: (a) a station for having a subject perform a motion; (b) a station for measuring the subject's motion; (c) a station for quantitatively characterizing the subject's measured motion to generate a movement signature; (d) a station for comparing the subject's movement signature to a normative value for a movement signature derived from control subjects performing the same motion; and (e) a station for having the subject observe a virtual environment while performing the motion to influence the subject's motion so as to align the subject's movement signature more closely to the normative movement signature.

In some embodiments, the present invention comprises a computer readable medium for performing the method comprising: (a) program code for measuring a subject's motion; (b) program code for quantitatively characterizing the subject's measured motion to generate a movement signature; (c) program code for comparing the subject's movement signature to a normative value for a movement signature derived from control subjects performing the same motion; (d) program code for manipulating a virtual environment while a subject performs the motion to influence the subject's motion so as to align the subject's movement signature more closely to the normative movement signature; and (e) program code for measuring change of the subject's movement signature.

In some embodiments, the present invention provides a method of virtual reality training for a subject, comprising: (a) having a subject perform a movement, wherein the subject's movement can be quantified as a movement signature; (b) comparing the subject's movement signature to a normative value movement signature derived from control subjects performing the same movement; (c) having a subject perform a movement while observing a virtual environment, wherein the virtual environment comprises a normative value movement signature derived from control subjects performing the same movement; and (d) having the subject attempt to synchronize the subject's movement to the virtual environment.

The invention will now be described with reference to the drawing figures, in which like reference numerals refer to like parts throughout. The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Embodiments of the disclosed invention encompass the paradigm shift toward physiological and behavioral measurement techniques that can index dynamical diseases. This shift challenges the premise that behavioral variability is adverse to healthy functioning—a prominent assumption in clinical locomotor research, for example (e.g., Blin, Ferrandez, & Serratrice, *J Neurol Sci*. 98: 91-7, 1990; Grabiner, Biswas, & Grabiner, *Arch Phys Med Rehabil*. 2001; Owings & Grabiner, *J. Biomech.* 2004; Spaulding, Livingston, & Hartsell, *Gait Posture* 2003; von Porat et al. *Knee Surg Sports Traumatol Arthrosc* 14:546-554, 2006; Webster, Merory, & Wittwer, *Alzheimer Dis Assoc Disord*. 2006). A central tenet of the approach prescribed by the present invention is that the system's dynamics (for example, continuously measured locomotor patterns) are more revealing in combination with classic summary measures of performance, compared to the summary measures alone.

In order to measure the system dynamics of the disclosed invention, some embodiments provide a unique classification of mathematics employed to prescribe certain patterns which corresponds to the movement of a test subject. By way of example, the movement may include, but is not limited to, the gait of a test subject. By mathematically describing the gait of a subject and transcribing that information into a movement signature or pattern, one may capture the characterized information electronically for subsequent analysis and/or processing. Thus, one may mathematically capture the gait pattern for a healthy subject. Alternatively, one may also mathematically capture the gait pattern for an unhealthy subject. The respective patterns for both the healthy and unhealthy subjects may be compared and utilized, as described herein. For example, knowing the differences in movement signatures between a healthy and unhealthy adult gait, a movement signature of a healthy adult gait may be altered to mimic an unhealthy adult gait movement signature perhaps affected by a neurological insult such as one resulting from injury, aging, or disease.

Embodiments of the disclosed invention allow VR to play an important role as a research tool for analyzing movement. Specifically, VR enables the control of visual information and feedback that constrains or alters a movement pattern. This offers the flexibility to manipulate visual stimuli during that movement (e.g. gait) in a particular manner to influence the pattern of variability exhibited by the individual's movement pattern (e.g. gait cycle). It can also be used to constrain the locomotor trajectories exhibited by patients (e.g. during over-ground walking). In other words, according to disclosed embodiments, VR is used to modify control parameters, thereby allowing researchers to test specific predictions about the role of those parameters in clinical assessment. These behaviors are a result of complex interactions at various control levels. Consequently, the examination of the various control parameters must take place at multiple scales of observation to fully understand the system dynamics. Described embodiments are provided that focus on several novel VR applications for the assessment of functional mobility at differing scales of observation.

Disclosed embodiments provide synchronizing to a stimulus as a method used to influence the timing properties of motor behavior. Embodiments of the invention demonstrate that more efficient adaptation to a perturbation (i.e., visual or auditory disruption to the synchronizing rhythm) occurs when participants synchronize to a visual stimulus. Accordingly, the invention determines the privileged role visual information plays in the modification of acute changes to the gait cycle in healthy elderly adults. Given the biological nature of human gait, introducing a natural pattern of variability in the synchronizing stimuli is determined to lead to a more adaptive gait pattern and enhanced functional mobility.

For example, it is determined that variability in the gait cycle, once thought to be a random by-product of locomotor control, reflects adaptive, functional gait. Specifically, the variation in the stride-to-stride intervals of healthy adults exhibits scale invariant (fractal) temporal correlations as indexed, for example, by detrended fluctuation analysis (DFA). The method of detrended fluctuation analysis has proven useful in revealing the extent of patterns in time series. Briefly, the time series to be analyzed (with N samples) is first integrated.

Prior to the removal of non-stationarity (i.e., detrending the data), the time series is first integrated by subtracting the mean from every data point through the following equation:

$$y(k) = \Sigma_{i=1}^{k}[S(i) - S_{ave}],$$

where S(i) is the ith step number and $S_{ave}$ is the average step interval and k is the number of data points in the time series.

Next, the integrated time series is divided into boxes of equal length, n. In each box of length n, a least squares line is fit to the data (representing the trend in that box). The y coordinate of the straight line segments is denoted by $y_n(k)$. A similar analysis can be done with other movement patterns, such as, but not limited to, movements of the arm, leg, hand, foot, digits, head, or other body parts.

Next, the integrated time series, y(k), can be detrended by subtracting the local trend, $y_n(k)$, in each box. The root-mean-square fluctuation of this integrated and detrended time series is calculated by $$F(n) = \sqrt{\frac{1}{N}\sum_{k=1}^{N}[y(k) - y_n(k)]^2}.$$

This computation can be repeated over all time scales (box sizes) to characterize the relationship between F(n), the average fluctuation, and the box size, n. Typically, F(n) will increase with box size. A linear relationship on a log-log plot indicates the presence of power law (fractal) scaling. Under such conditions, the fluctuations can be characterized by a scaling exponent, the slope of the line relating log F(n) to log n.

Thus, the DFA analysis may be incorporated into the algorithm utilized by the disclosed embodiment to measure and determine a movement signature for describing the gait pattern of a subject. Once captured, the aforementioned movement signature may be analyzed or further processed as described herein. Skilled artisans within the same technical field of endeavor will readily appreciate that other suitable mathematical concepts may be employed by the invention for determining movement signatures.

In select embodiments, humans may be required to synchronize to a variable, or "noisy", visual metronome, to, thereby, enhance adaptive variation in their gait. A noisy metronome produces irregular intervals—some are shorter and some are longer than the previous one. A fractal pattern of dynamic variability can be generated to reflect movement observed in healthy human gait. Instructing a patient to synchronize to a noisy metronome may induce desired patterns of dynamic variability in their gait cycle, enhancing adaptive functional mobility.

The present invention determines that the structure of variability of a movement task can be manipulated by altering the dynamic properties of a visual stimulus. For example, this methodology can be applied to the gait domain to determine that shifts in gait dynamics may be elicited in a desired direction. For example, in early trials, participants may synchronize their steps to a flashing square on a computer screen while walking on a treadmill. The visual metronome may generate intervals with a variety of temporal patterns (indexed by DFA). Visual metronomes may be incorporated into VR training via inclusion in a virtual environment.

The participants' stride-to-stride intervals may then shift in the prescribed direction from a stochastic structure of variability that tends toward pink noise, to one that is influenced by either greater or lesser degrees of randomness (i.e., exhibiting either a more random, white noise structure, or alternatively an even more correlated, pink noise structure, respectively) as a result of VR training. This result can provide an analysis of the efficacy of using noisy visual metronomes to manipulate the nonlinear dynamics of the gait cycle, that may enhance functional mobility.

The VR visual stimuli may be presented using either discrete or continuous information. A discrete visual stimulus (i.e., a classic visual metronome) only prescribes the time when an event should occur (e.g., a heel-strike during locomotion). A continuous visual stimulus, on the other hand, provides information that anticipates and specifies the timing of the upcoming event (e.g., motion of the foot and/or limb leading to and including a heel-strike). While both discrete and continuous stimuli have been shown to be useful, a continuous stimulus, according to the disclosed invention, may enable a participant to more precisely synchronize to irregular events. Coupled with one or more VR platforms, some disclosed embodiments provide VR to present novel classes of stimuli, such as virtual humans and/or avatars to provide discrete or continuous information.

A distinction is made about the origin of the discrete or continuous information as it pertains to the present invention. Disclosed embodiments provide that if a computer algorithm drives the character in virtual reality (e.g., as described herein), then it can present discrete and/or continuous information about walking biomechanics that is non-biological and is termed a virtual human. Alternatively, disclosed embodiments may provide that the character can be driven by the actual motion of a human in either real-time or via a recording, which is deemed biological motion and termed an avatar. Determinations may be made to distinguish which type of motion is optimal for a gait synchronization task, as deemed necessary.

It is therefore possible to exhibit a number of ways that discrete or continuous information, for example, that directed to a desired gait pattern, may be exhibited to a patient. For example, the movement signature, discussed above, may be inputted into a VR platform to produce a visual image of movement pattern. In one example, the area of interest may relate to a gait pattern. While a gait pattern is instantly described, it is readily appreciated that other physical movements of human extremities may be captured by the present invention.

Figure 1:
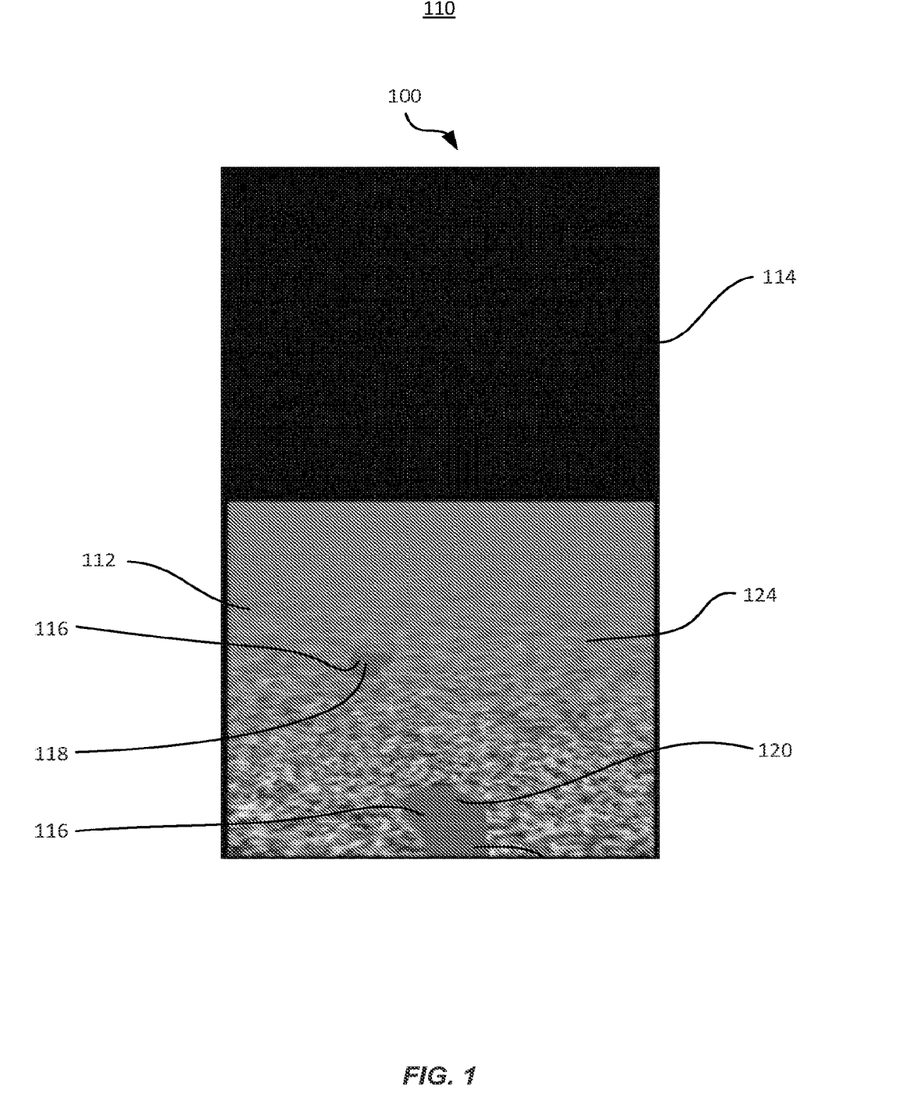
FIG. 1 illustrates a virtual environment according to one embodiment of the present invention.

Turning to FIG. 1, a virtual image 100 is illustrated depicting a virtual environment 110. As such, a surface area 112 and background 114 is shown in the imaging. Surface area 112 may be configured to continuously move towards a user as they view virtual image 100. As surface area 112 scrolls towards the user, embedded footprints 116 may generate on virtual image 100 at prescribed locations and time intervals. Footprints 116 represent a users foot signature against surface area 112 including the physical dynamics of a foot structure such as a heel area 118 and a toe area 120. Thus, footprints 116 may continuously move through virtual environment 110, providing visual information about the timing leading up to a heel strike.

Footprints 116 may be configured to retrace a user's steps and may be prescribed with the movement signature captured by the disclosed algorithm for a prescribed gait. In a select embodiment, the gait may correspond to a healthy gait of an adult test subject. Thus, the pattern of footprints 116 that appear on virtual environment 110 may correspond to the walking strides of the aforementioned test subject including, for example, the intricacies and fluctuations in speed, stride length, placement, etc. In the current embodiment, two footprints are shown as surface area 112 scrolls forward. As the closest footprint eventually disappears in the proximal area 120, another footprint emerges in the distal area 124 to give the illusion that someone is walking forward on surface area 112.

Virtual image 100 may be used in combination with additional equipment in accordance with disclosed embodiments. For example, virtual image 100 may be configured as a display in front of a treadmill. The treadmill may be configured to virtual image 100 such that the speed of the movable surface track of the treadmill corresponds to the relative movement of surface area 112 scrolling towards the user. Thus, a user may operate the treadmill and attempt to mimic footsteps 116 at the same timing and location points on the treadmill surface. Because footsteps 116 appear at select locations and time intervals, the user is required to do some planning in order to mimic similar actions with their respective footsteps. Accordingly, a user may self select a speed (e.g., 3 mph), of the treadmill. Virtual surface area 112 is configured to correspond to move at the same speed as the movable surface track of the treadmill. The user will receive an optic flow or visual field that is moving towards them in a virtual environment.

By creating virtual footsteps 116 and programming them to mimic a healthy continuous gait pattern, persons with unhealthy gait patterns (e.g., due to an injury such as a structural or neurological insult) may attempt to mimic a healthy gait pattern as an innovative way to enhance their rehabilitation. In this manner, disclosed embodiments focus on developing VR applications to aid in physical therapy—specifically, in retraining patients how to walk after an injury. Because the healthy examples of footsteps 116 continuously appear in virtual environment 110, patients may receive flawless examples and visual stimulations during their rehabilitation process.

An expansion of the locomotive gait may include visually representing a person in the virtual environment. For example, turning to FIG. 2, virtual image 200 illustrates a virtual environment 202. A surface area 204 and background 206 is shown in the imaging. Again, surface area 204 may be configured to continuously move towards a user as they view virtual image 200. As surface area 204 scrolls towards the user, a stick FIG. 208 walks along surface area 204. To enhance visual perception, a side view 210 of stick FIG. 208 may also be provided. Movement of stick FIG. 208 in side view 210 will correspond to movement of stick FIG. 208 in the main view 212. One or more extremities of stick FIG. 208 may be programmed to mimic the movement signature, e.g., as discussed above, to produce a visual image of a movement pattern for that respective extremity. Extremities 214 may include, for example, respective upper leg, respective lower leg, respective feet, respective upper arms, respective lower arms etc. Thus, as surface area 204 scrolls forward, stick FIG. 208 walks within virtual environment 202. Each extremity 214 may be programmed to move accordingly, for example, in time and at a disclosed location. Advantages afforded by providing stick FIG. 208 to walk through a virtual landscape include, for example, providing information to the patient/user about joint angles in the different phases of the gait cycle.

Figure 2:
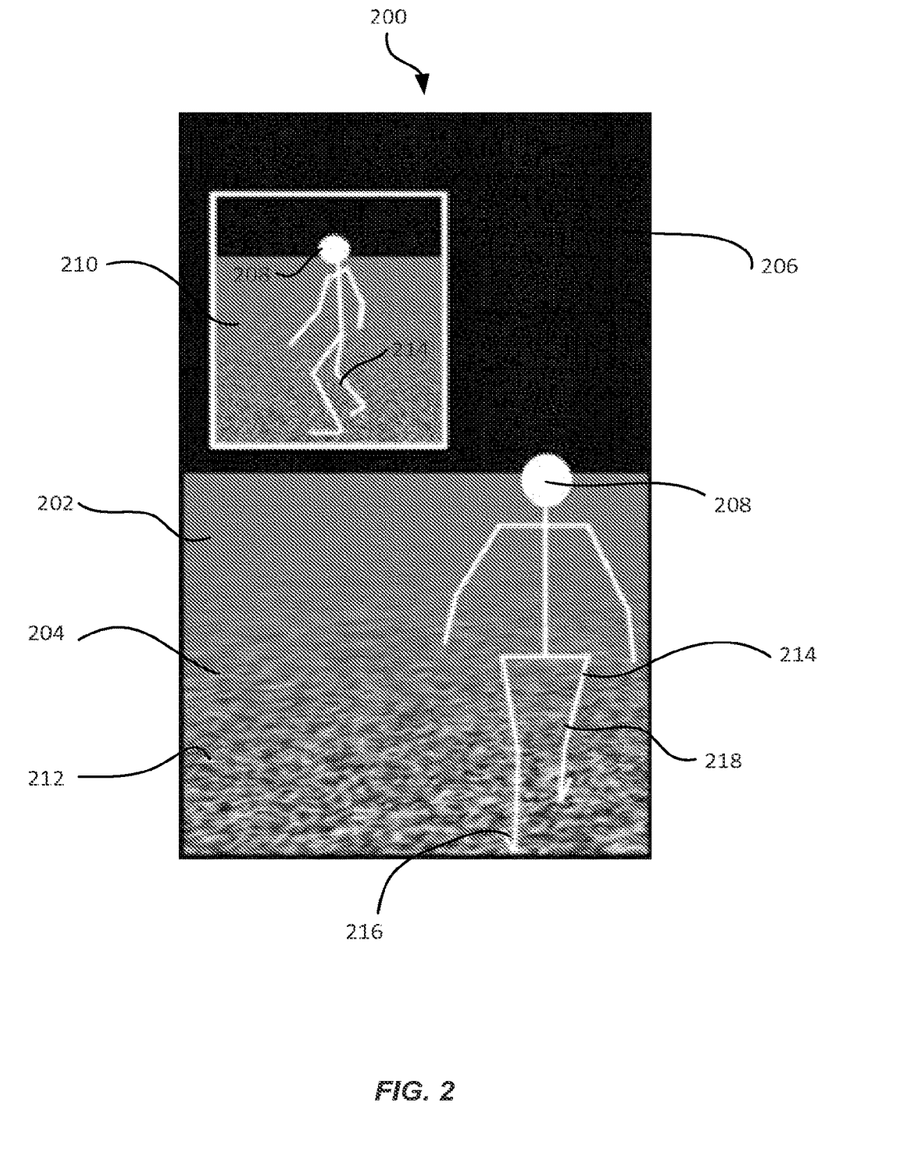
FIG. 2 illustrates a virtual environment according to another embodiment of the present invention.

Extremities 214 may be configured to retrace the movement of a user's steps and may be prescribed with the movement signature captured by the disclosed algorithm for a prescribed gait. In a select embodiment, the gait may correspond to a healthy gait of an adult test subject. Thus, the pattern of extremities, for example, foot placement 216 and/or leg positioning 218 that appear on virtual environment 202 may correspond to the walking strides of the aforementioned test subject including, for example, the intricacies and fluctuations in speed, stride length, placement, etc.

As with virtual image 100, virtual image 200 may be used in combination with additional equipment, such as a treadmill, in accordance with disclosed embodiments. Placed in front of a treadmill, virtual image 200 may be configured with the treadmill scroll surface area 204 in accordance with the same speed of the movable surface track of the treadmill. Thus, a user may operate the treadmill and attempt to synchronize movements with the movement of the extremities 214 of stick FIG. 208 at the same timing and location points on the treadmill surface. Because extremities 214 appear at select locations and time intervals, the user is required to do some planning in order to synchronize similar actions with their respective footsteps to those of the stick FIG. 208. Accordingly, a user may self select a speed, e.g., 3 mph, of the treadmill. Virtual surface area 204 is configured to correspond to move at the same speed as the movable surface track of the treadmill. The user will receive an optic flow or visual field that is moving towards them in a virtual environment.

By creating virtual extremities 214 and programming them to mimic a healthy continuous gait pattern, persons with unhealthy gait patterns (e.g., due to an injury such as a structural or neurological insult) may attempt to mimic a healthy gait pattern as an innovative way to enhance their rehabilitation. In this manner, disclosed embodiments focus on developing VR applications to aid in physical therapy—specifically, in retraining patients how to walk after an injury. Because the healthy examples of extremities 214 continuously appear in virtual environment 202, patients may receive flawless examples and visual stimulations during their rehabilitation process.

Disclosed concepts may also be expanded to include programming avatars, for example representing a humanoid figure, which mimic the movement signature, discussed above, to produce a visual image of a movement pattern. For example, turning to FIG. 3, virtual image 300 illustrates a virtual environment 302. A surface area 304 and background 306 is shown in the imaging. Again, surface area 304 may be configured to continuously move towards a user as they view virtual image 300. As surface area 304 scrolls towards the user, an avatar 308 walks along surface area 304. To enhance visual perception, a side view 310 of avatar 308 may also be provided. Movement of avatar 308 in side view 310 will correspond to movement of avatar 308 in the main view 312. One or more extremities of avatar 308 may be programmed to mimic the movement signature, e.g., as discussed above, to produce a visual image of a movement pattern for that respective extremity. Extremities 314 may include, for example, respective upper leg, respective lower leg, respective feet, respective upper arms, respective lower arms etc. Thus, as surface area 304 scrolls forward, avatar 308 walks within virtual environment 302. Each extremity 314 may be programmed to move accordingly, for example, in time and at a disclosed location.

Figure 3:
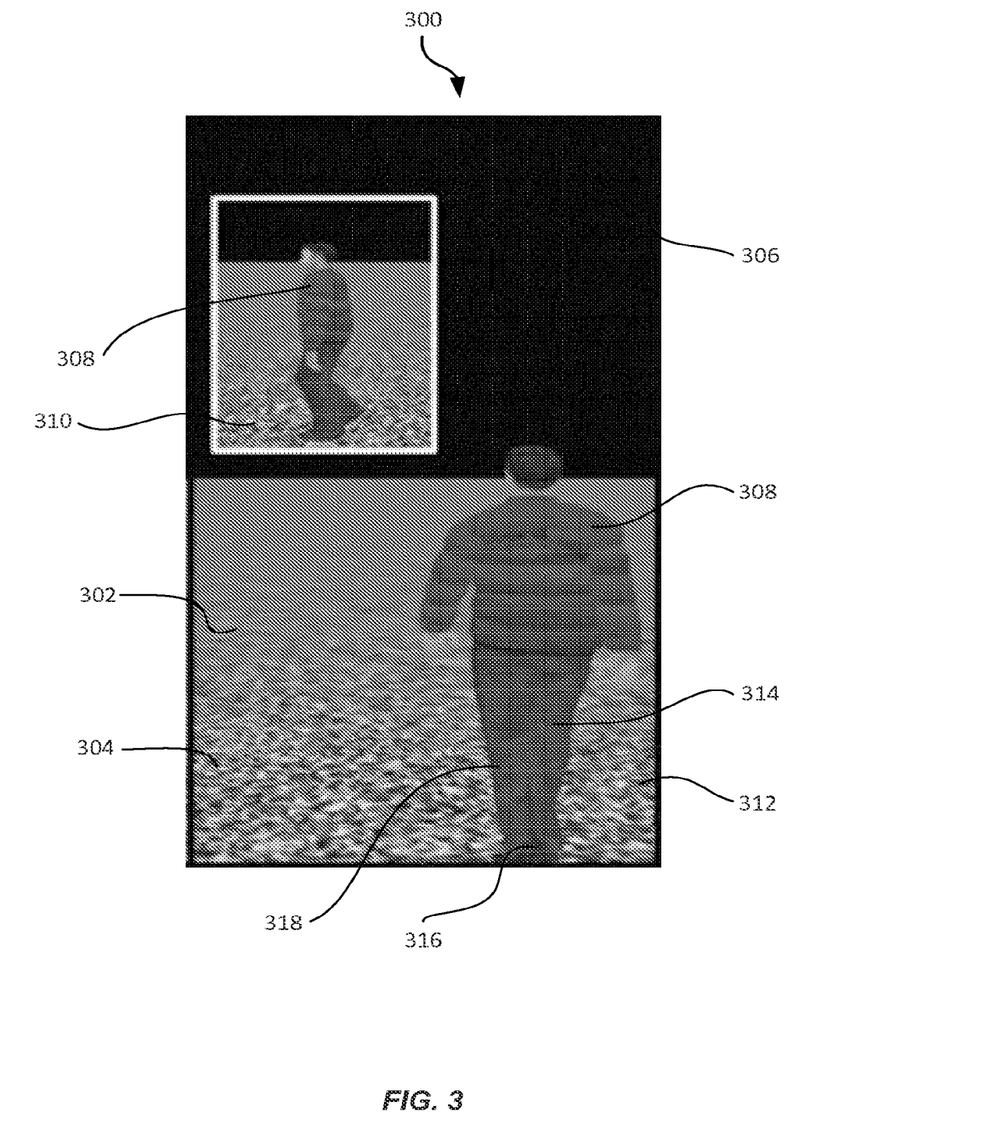
FIG. 3 illustrates a virtual environment according to yet another embodiment of the present invention.

Extremities 314 may be configured to retrace the movement of a user's steps and may be prescribed with the movement signature captured by the disclosed algorithm for a prescribed gait. In a select embodiment, the gait may correspond to a healthy gait of an adult test subject. Thus, the pattern of extremities, for example, foot placement 316 and/or leg positioning 318 that appear on virtual environment 302 may correspond to the walking strides of the aforementioned test subject including, for example, the intricacies and fluctuations in speed, stride length, placement, etc.

As with virtual images 100 and 200, virtual image 300 may be used in combination with additional equipment, such as a treadmill, in accordance with disclosed embodiments. Placed in front of a treadmill, virtual image 300 may be configured with the treadmill scroll surface area 304 in accordance with the same speed of the movable surface track of the treadmill. Thus, a user may operate the treadmill and attempt to synchronize his or her movement with the movement of the extremities 314 of avatar 308 at the same timing and location points on the treadmill surface. Because extremities 314 appear at select locations and time intervals, the user is required to do some planning in order to mimic similar actions with their respective footsteps. Accordingly, a user may self select a speed, e.g., 3 mph, of the treadmill. Virtual surface area 304 is configured to correspond to move at the same speed as the movable surface track of the treadmill. The user will receive an optic flow or visual field that is moving towards them in a virtual environment.

By creating virtual extremities 314 and programming them to mimic a healthy continuous gait pattern, persons with unhealthy gait patterns (e.g., due to an injury such as a structural or neurological insult) may attempt to mimic a healthy gait pattern as an innovative way to enhance their rehabilitation. In this manner, disclosed embodiments focus on developing VR applications to aid in physical therapy—specifically, in retraining patients how to walk after an injury. Because the healthy examples of extremities 314 may continuously appear in virtual environment 302, patients may receive flawless examples and visual stimulations during their rehabilitation process. Thus, in certain embodiments a humanoid figure would be even more salient for synchronization purposes, so high-definition virtual humans or avatars may be an appropriate choice.

Thus, certain embodiments may provide dual virtual footsteps 116, stick FIGS. 208 or virtual humans or avatars 308 represented on virtual images 100, 200 and 300, respectfully. The dual virtual footsteps 116, stick FIGS. 208 or virtual humans or avatars 308 may be presented with one character driven by the continuous information (desired movement) and the other character configured to a patient/user. As the patient/user attempts to mimic the movements of the virtual footsteps 116, stick FIGS. 208 or virtual humans or avatars 308, the other set of footsteps 116, stick FIGS. 208 or virtual humans or avatars 308, coupled directly to the movements of the patient/user, will be displayed. If the movements did or did not correspond, for example, to the healthy gait movement, the patient/user may have instant visual feedback about their own performance, but would provide a model character for real-time movement comparisons.

In embodiments utilizing DFA, a value of 0.50 represents random movement while 1.0 represents perfectly regular movement. In selecting a goal for regularity of movement for a given subject (i.e. a target value for DFA), any DFA value that is closer to 0.75 than the baseline value for that subject may be appropriate. For example if the starting (baseline) DFA is 0.50, an appropriate DFA value which may be reflected in a visual stimulus (e.g. in a virtual environment) may be in the range of 0.55-1.0. If the starting DFA value is 1.0, an appropriate DFA value may be in the range of 0.5-0.95.

In embodiments where VR training sessions are repeated until a desired result is attained, it may be appropriate to select a predetermined value for which a change in a subject's motion may represent successful completion of training Such a DFA value may be in the range of 0.70-0.80, 0.69-0.81, 0.68-0.82, 0.67-0.83, 0.66-0.84, 0.65-0.85, or even broader or narrower ranges depending on the restrictions of the subject. Those skilled in the art will recognize that evaluation of the challenges and circumstances for each individual subject is appropriate to determine such a predetermined value of DFA at which training may cease if achieved by the subject during VR training. Having attained a movement signature representing a predetermined goal value, a subject may continue to exhibit movement corresponding to the goal movement signature value even after VR training is discontinued.

Figure 4:
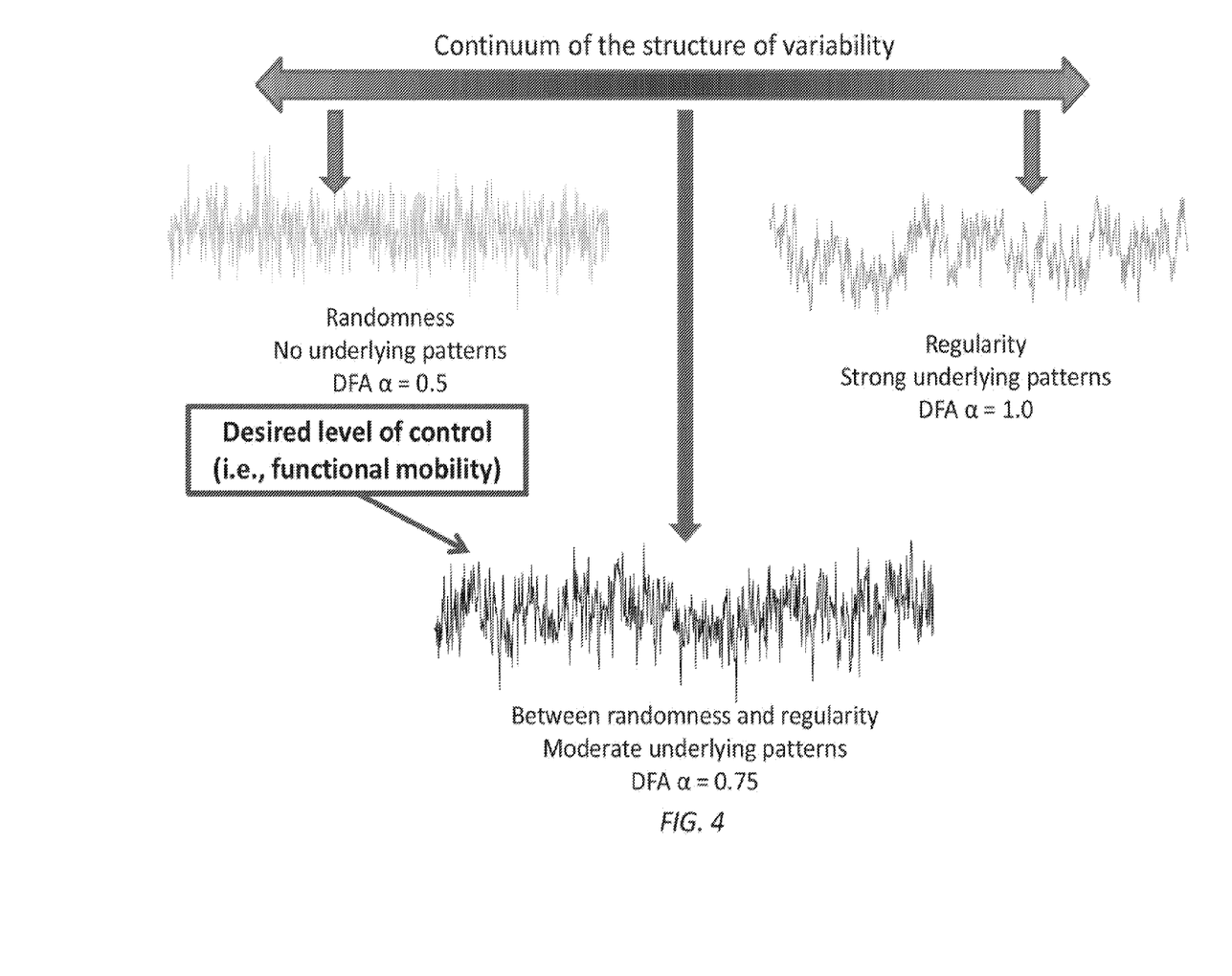
FIG. 4 illustrates a continuum of the structure of variability according to an embodiment of the present invention.

FIG. 4 illustrates the continuum between randomness and regularity and the values reflected by DFA. Randomness (i.e. no underlying pattern) is reflected by lower DFA values, while regularity (i.e. strong underlying pattern) is reflected by higher DFA values. A subject having a mobility deficit may begin with movements reflecting a DFA value representing more random movement (i.e. lower DFA value). Following virtual reality training according to an embodiment of the present invention, the movements may become more regular such that they are reflected by a higher DFA value. Alternatively, if a subject's starting DFA value represents a more regular movement (i.e. higher DFA value), the movements may become more random.

Figure 5:
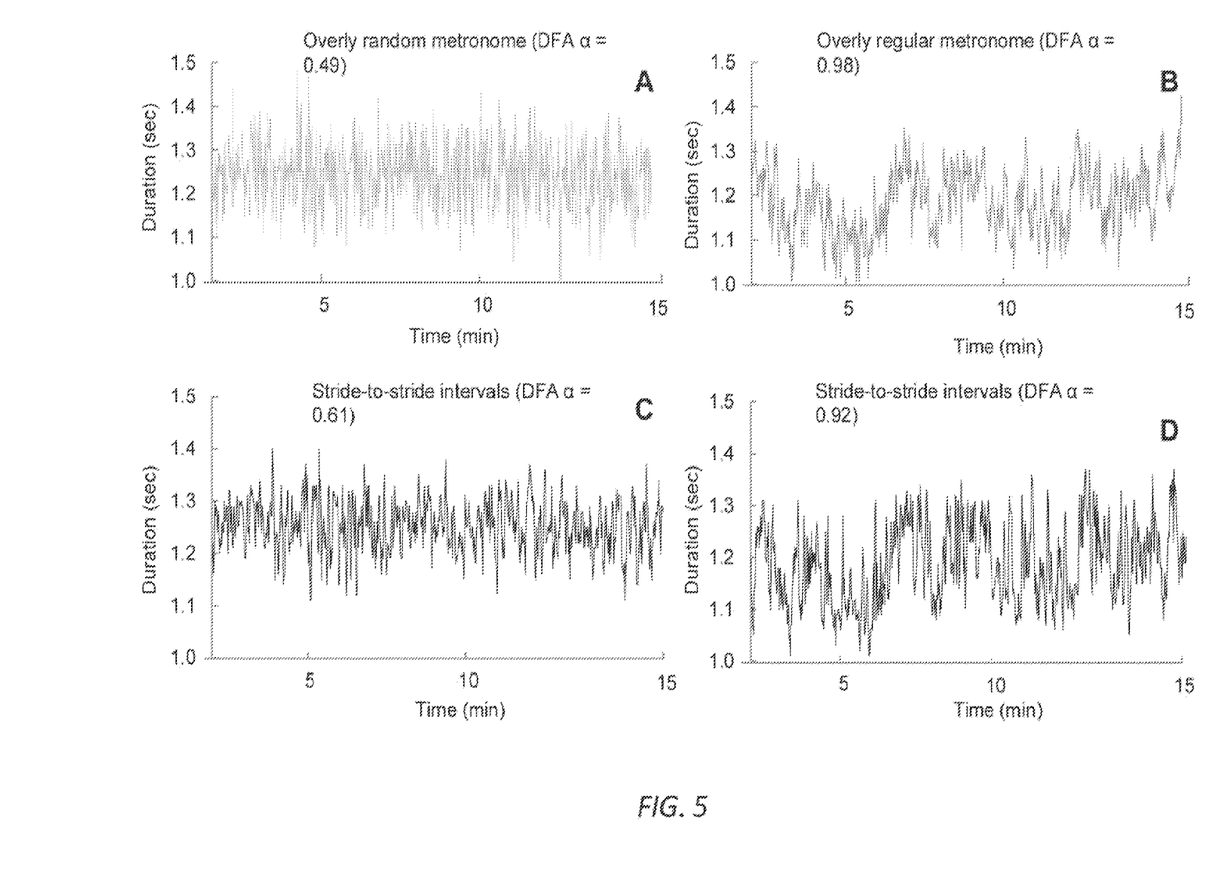
FIG. 5 illustrates a time series for stride-to-stride intervals influenced by visual metronome according to an embodiment of the present invention.

FIG. 5 demonstrates the time series for the visual metronome with overly random (A) or overly regular (B) patterns and the corresponding gait behavior responses (C and D, respectively) are shown. Qualitatively, the dynamics in the visual metronome time series were reproduced in the gait dynamics (A and C are similar; B and D are similar). This observation was confirmed quantitatively by examining the DFA $\alpha$ values for the gait dynamics in each condition. This participant's baseline condition (no visual metronome; not shown) DFA $\alpha$ was 0.76 and moved toward more random (C, DFA $\alpha$=0.61) or more regular (D, DFA $\alpha$=0.92) behavior in the two metronome conditions.

Advantages of the disclosed VR embodiment is that it provides a platform for the development of unique and customizable interventions that are not available or easily implemented in the real world. Specifically, VR enables the manipulation of training duration, intensity and feedback paralleling clinical demands for intensive and repetitive patient training. When developing VR interventions, important considerations are made for both the construction of the virtual environments and the interfacing measurement and feedback systems that accompany them. By selectively inputting algorithms into the disclosed VR environment to capture movement signatures in the specified manner, patients will be able to synchronize their movements to mimic prescribed movements thereby making their rehabilitation process more effective and efficient.

As disclosed herein, the movement signatures of the disclosed embodiment can provide a quantitative measurement of healthy or unhealthy locomotor patterns or movements. This is due to the virtual environment being built to include the locomotor patterns or movements, such as healthy gait biomechanics, with incorporating particular patterns corresponding to prescribed movement signatures as disclosed by the present invention. By building the patterns generated from the movement signatures into the described virtual environment, the present invention can provide a more specified training course to rehabilitate an injured patient. This may be done, for example by comparing a healthy locomotor pattern or movement, such as a gait, with an unhealthy locomotor pattern or movement. Because measurements are performed on a continuum to show what is wrong with a person due to their structural or neurological insult, a quantifiable measurement is able to be obtained to show where the progress of the patient is on the continuum. This capability will not only show the progress of the patient but will facilitate in knowing whether the patient has achieved certain thresholds or benchmarks to continue another or normal activity.

The disclosed invention may be implemented, for example, in VR platforms equipped with hi-speed motion capture cameras and VR software and/or open-source software applications including, for example, emergent technologies systems such as those provided by gaming devices under the trademarks of NINTENDO® WII™ (Nintendo Co. Ltd., Kyoto, Japan), MICROSOFT® KINECT® (Microsoft Corp., Redmond, Wash.) and PLAYSTATION® Move (Sony Computer Entertainment, Inc.). In some embodiments a VR device may be worn by a subject. Utilizing such systems, and others like them, may led to the widespread cost-effective availability of interactive VR and may provide new opportunities for the application of VR interventions both inside the home and in smaller clinical settings. Regardless, the implications of all of these technological enhancements have the potential to be far-reaching for clinical assessment and rehabilitation.

In at least one aspect, the invention provides a system for virtual reality training having (a) a station for having a subject perform a motion while visually observing a virtual environment; (b) a station for measuring the motion; (c) a station for quantitatively characterizing the measured motion to generate a movement signature; (d) a station for comparing the movement signature for the subject to a normative value for movement signature derived from control subjects performing the same motion; and (e) a station for manipulating the subject's virtual environment to influence the subject's motion so as to align the movement signature more closely to the normative movement signature. Such systems can include various embodiments and subembodiments analogous to those described above for methods of virtual reality training.

These systems may include various stations. As used herein, the term "station" is broadly defined and includes any suitable apparatus or collections of apparatuses suitable for carrying out the recited method. The stations need not be integrally connected or situated with respect to each other in any particular way. The invention includes any suitable arrangements of the stations with respect to each other. For example, the stations need not even be in the same room. But in some embodiments, the stations are connected to each other in an integral unit.

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

Figure 6A:
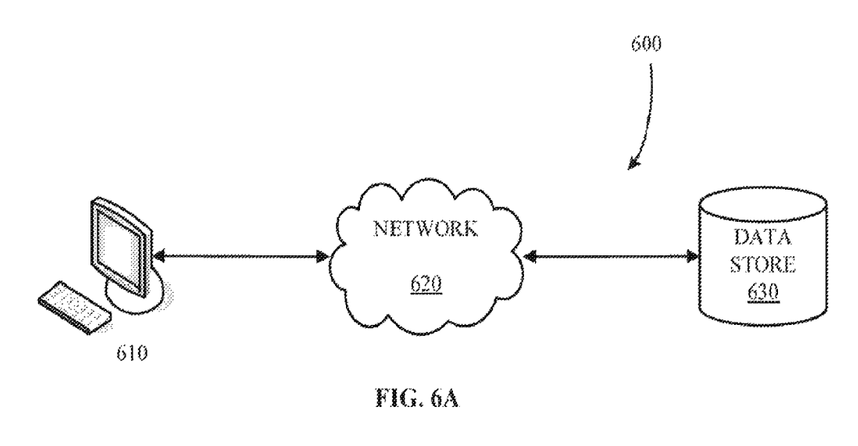
FIG. 6 illustrates embodiments of systems suitable for executing certain steps of the virtual reality training methods according to alternate embodiments of the present invention.
Figure 6B:
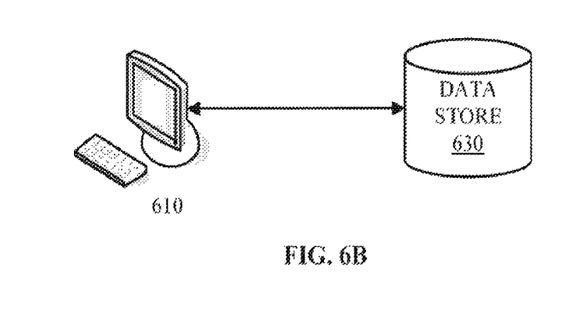

FIGS. 6A and 6B show embodiments of systems suitable for executing certain steps of the methods disclosed herein. For example, FIGS. 6A and 6B show diagrams depicting illustrative computing devices in illustrative computing environments according to some embodiments. The system 600 shown in FIG. 6A includes a computing device 610, a network 620, and a data store 630. The computing device 610 and the data store 630 are connected to the network 620. In this embodiment, the computing device 610 can communicate with the data store 630 through the network 620.

The system 600 shown in FIG. 6A includes a computing device 610. A suitable computing device for use with some embodiments may comprise any device capable of communicating with a network, such as network 620, or capable of sending or receiving information to or from another device, such as data store 630. A computing device can include an appropriate device operable to send and receive requests, messages, or information over an appropriate network. Examples of such suitable computing devices include personal computers, cell phones, handheld messaging devices, laptop computers, tablet computers, set-top boxes, personal data assistants (PDAs), servers, or any other suitable computing device.

In some embodiments, the computing device 610 may be in communication with other computing devices directly or through network 620, or both. For example, in FIG. 6B, the computing device 610 is in direct communication with data store 630, such as via a point-to-point connection (e.g. a USB connection), an internal data bus (e.g. an internal Serial ATA connection) or external data bus (e.g. an external Serial ATA connection). In one embodiment, computer device 610 may comprise the data store 630. For example, in one embodiment, the data store 630 may comprise a hard drive that is a part of the computer device 610.

In certain embodiments, a computer system may comprise a computer, an input device, a display unit, and/or the Internet. The computer further comprises a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit may allow the computer to connect to other databases and the Internet through an I/O interface. The communication unit may allow the transfer to, as well as reception of data from, other databases. The communication unit may include a modem, an Ethernet card, or any similar device which enables the computer system to connect to databases and networks such as LAN, MAN, WAN and the Internet. The computer system facilitates inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine. The system 600 shown in FIG. 6A includes a data store 630. The data store 630 can include several separate data tables, databases, or other data storage mechanisms and media for storing data relating to a particular aspect. It should be understood that there can be many other aspects that may need to be stored in the data store, such as to access right information, which can be stored in any appropriate mechanism or mechanisms in the data store 630. The data store 630 may be operable to receive instructions from the computing device 610 and obtain, update, or otherwise process data in response thereto.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

Figure 7A:
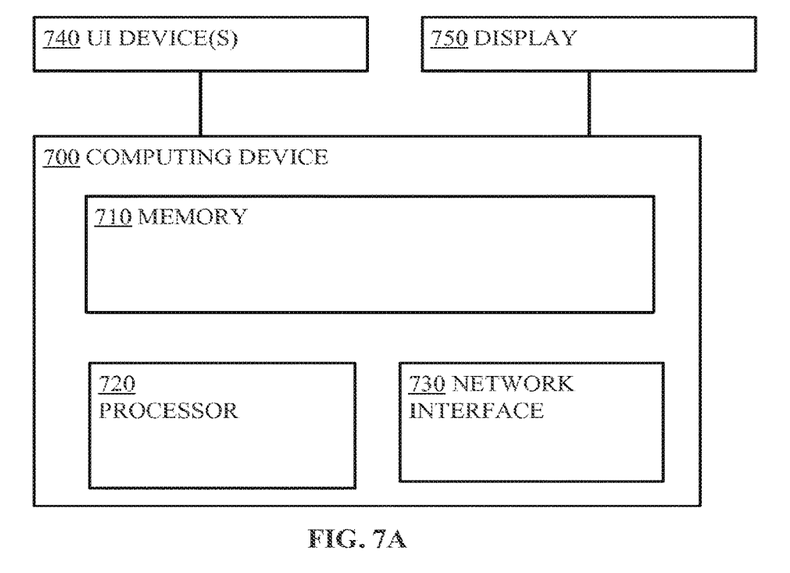
FIG. 7 illustrates block diagrams of computing devices according to various embodiments of the virtual reality training systems of the present invention.

FIGS. 7A and 7B show block diagrams depicting illustrative computing devices according to various embodiments. According to the embodiment shown in FIG. 7A, the computing device 700 comprises a computer-readable medium such as memory 710 coupled to a processor 720 that is configured to execute computer-executable program instructions (or program code) and/or to access information stored in memory 710. A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device 700 may comprise a single type of computer-readable medium such as random access memory (RAM). In other embodiments, the computing device 700 may comprise two or more types of computer-readable medium such as random access memory (RAM), a disk drive, and cache. The computing device 700 may be in communication with one or more external computer-readable mediums such as an external hard disk drive or an external DVD drive.

As discussed above, the embodiment shown in FIG. 7A comprises a processor 720 which is configured to execute computer-executable program instructions and/or to access information stored in memory 710. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device 700 comprises a single processor 720. In other embodiments, the device 700 comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Figure 7B:
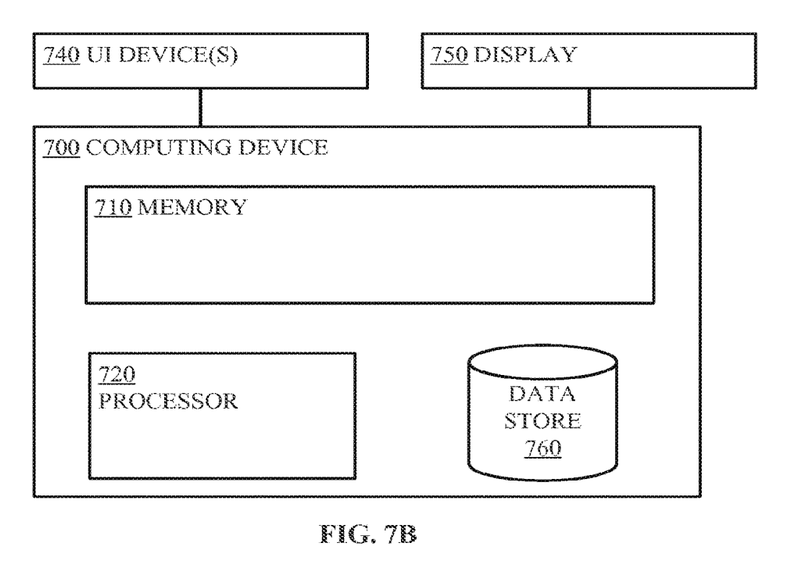

The computing device 700 as shown in FIG. 7A comprises a network interface 730. In some embodiments, the network interface 730 is configured for communicating via wired or wireless communication links. For example, the network interface 730 may allow for communication over networks via Ethernet, IEEE 802.11 (Wi-Fi), 802.16 (Wi-Max), BLUETOOTH®, infrared, etc. As another example, network interface 730 may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, such as the embodiment shown in FIG. 7B, the computing device may include a data store 760 in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device 700 shown in FIG. 7A is in communication with various user interface devices 740 and a display 750. Display 750 may use any suitable technology including, but not limited to, LCD, LED, CRT, and the like.

In various embodiments, suitable computing devices may be a server, a desktop computer, a personal computing device, a mobile device, a tablet, a mobile phone, or any other type of electronic devices appropriate for providing one or more of the features described herein. In at least one aspect, the invention provides systems for carrying out the analysis described above. Thus, in some embodiments, the present invention comprises a computer-readable medium on which is encoded programming code for the generalized ridge regression methods described herein. Also in some embodiments, such as described above with respect to FIGS. 6 and 7, the invention comprises a system comprising a processor in communication with a computer-readable medium, the processor configured to perform the generalized ridge regression methods described herein. Suitable processors and computer-readable media for various embodiments of the present invention are described in greater detail above.

In at least one aspect, the invention provides computer readable media for virtual reality training according to the present invention. Such computer readable media can include various embodiments and subembodiments analogous to those described above for methods of validating a binding assay, including other embodiments of methods described throughout this specification.

In at least one aspect, the computer readable media allow input data from various stations. Each of these stations can include various detection methods, and data are generated from each of the detections. These data can be collected, amplified, and converted to digital form, and then may be compiled and/or transformed, if necessary, using any standard spreadsheet software such as Microsoft Excel, FoxPro, Lotus, or the like, or standard statistical algorithms. In an embodiment, the data are entered into the system for each subject and/or stored in memory. Alternatively, data from previous subjects are stored in the computer memory and used as required. In an embodiment data from control subjects are compiled to generate normative values for measurement signature.

At each point in the analysis, the user may input instructions via a keyboard, floppy disk, flash memory, remote access (e.g., via the Internet), or other access means. The user may enter instructions including options for the run, how reports should be printed out, and the like. Also, at each step in the analysis, the data may be stored in the computer using a storage device common in the art such as disks, drives or memory. As is understood in the art, the processor and I/O controller are required for multiple aspects of computer function. Also, in an embodiment, there may be more than one processor, wherein each processor is configured to perform some portion of a method disclosed by this specification and such processors are in communication with each other or another processor.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming Physionet.org is a resource for algorithms, MATLAB functions, and open source software related to physiology applications. The processing of input data by the processing machine may be in response to user commands, results of previous processing, or a request made by another processing machine.

Having described the many embodiments of the present invention in detail, it will be apparent that modifications and variations are possible without departing from the scope of the present invention defined in the appended claims. Furthermore, it should be appreciated that all examples in the present disclosure, while illustrating many embodiments of the present invention, are provided as non-limiting examples and are, therefore, not to be taken as limiting the various aspects so illustrated.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof. References cited herein are also incorporated by reference as though fully set forth herein.

I claim:

1. A method of virtual reality training for a subject, comprising:
    (a) having a subject perform a motion;
    (b) measuring the fractal pattern of the subject's motion over time using a computer;
    (c) comparing the measurement of the fractal pattern of the subject's motion to a normative value for fractal pattern of the same motion performed by control subjects;
    (d) providing a virtual environment based on the comparison in (c) to influence the subject's motion so as to align the subject's motion more closely to the motion derived from control subjects; wherein the virtual environment comprises a stimulus having a fractal pattern that is closer to the normative fractal pattern than is the fractal pattern of the subject's motion;
    (e) instructing the subject to synchronize his or her motion to the stimulus in the virtual environment; and
    (f) repeating steps (a)-(e) until the measurement of fractal pattern of the subject's motion reaches a predetermined value.

2. The method of claim 1, wherein the subject is instructed to synchronize the motion to a visual stimulus observed in the virtual environment, wherein the visual stimulus generates intervals with a variety of temporal patterns.

3. The method of claim 1, wherein the measurement of fractal pattern over time comprises an integrated time series.

4. The method of claim 3, wherein the integrated time series is indexed by detrended fluctuation analysis.

5. The method of claim 1 or 2, wherein the subject has a mobility deficit due to a neurological or structural insult.

6. The method of claim 1 or 2, wherein the motion is a locomotor motion.

7. The method of claim 6, wherein the locomotor motion is walking.

8. The method of claim 6, wherein the locomotor motion is running.

9. The method of claim 5, wherein the subject is in need of rehabilitation for functional mobility.

10. The method of claim 1 or 2, wherein the virtual reality training facilitates recovery of the subject's functional mobility.

11. The method of claim 2, wherein the visual stimulus comprises discrete visual cues in the virtual environment.

12. The method of claim 2, wherein the visual stimulus comprises continuous visual cues in the virtual environment.

13. The method of claim 11 or 12, wherein the visual stimulus comprises an avatar.

14. The method of claim 11 or 12, wherein the visual stimulus comprises a visual metronome.

15. The method of claim 2, wherein the motion is walking and the subject is instructed to synchronize heel strikes to the visual stimulus.

16. The method of claim 6, wherein the subject performs the locomotor motion on a treadmill.

17. The method of claim 6, wherein the subject performs the locomotor motion over ground.

18. The method of claim 1, wherein the subject observes the virtual environment through a device worn by the subject.

19. A non-transitory computer readable medium for performing a method comprising:
    (a) program code for instructing a subject to perform a motion;
    (b) program code for measuring the fractal pattern of a the subject's motion over time;
    (c) program code for comparing the fractal pattern of the subject's motion to a normative fractal pattern of the same motion performed by control subjects;
    (d) program code for manipulating a virtual environment while the subject performs the motion to influence the subject's motion so as to align the subject's motion more closely to the motion derived from control subjects; wherein the manipulation comprises providing a stimulus having a fractal pattern that is closer to the normative fractal pattern of the motion than is the fractal pattern of the subject's motion; and
    (e) program code for instructing the subject to synchronize his or her motion to the stimulus in the virtual environment; and
    (f) program code for repeating steps (a)-(e) until the measurement of fractal pattern of the subject's motion reaches a predetermined value.

* * * * *